(12) United States Patent
Sandin et al.

(10) Patent No.: US 7,172,585 B2
(45) Date of Patent: Feb. 6, 2007

(54) ABSORBENT PRODUCT

(75) Inventors: Cécile Sandin, Mölndal (SE); Lennart Nilsson, Skärhamn (SE)

(73) Assignee: SCA Hygiene Products AB, Gothenburg (SE)

( * ) Notice: Subject to any disclaimer, the term of this patent is extended or adjusted under 35 U.S.C. 154(b) by 442 days.

(21) Appl. No.: 10/179,273

(22) Filed: Jun. 26, 2002

(65) Prior Publication Data

US 2003/0014029 A1 Jan. 16, 2003

Related U.S. Application Data

(60) Provisional application No. 60/302,365, filed on Jul. 3, 2001.

(51) Int. Cl.
*A61F 13/20* (2006.01)

(52) U.S. Cl. .............................. 604/385.3; 604/385.01

(58) Field of Classification Search ........... 604/385.01, 604/385.3, 385.02–385.101, 385.11–385.29
See application file for complete search history.

(56) References Cited

U.S. PATENT DOCUMENTS

| | | | |
|---|---|---|---|
| 4,037,602 A * | 7/1977 | Hawthorne | 604/375 |
| 4,938,757 A | 7/1990 | Van Gompel et al. | |
| 5,628,737 A | 5/1997 | Dobrin et al. | |
| 5,749,866 A * | 5/1998 | Roe et al. | 604/385.24 |
| 5,785,699 A * | 7/1998 | Schmitz | 604/391 |
| 6,086,571 A * | 7/2000 | Guevara et al. | 604/385.29 |
| 6,241,716 B1 * | 6/2001 | Ronnberg | 604/391 |
| 6,352,607 B1 * | 3/2002 | Kuen et al. | 156/227 |

| | | |
|---|---|---|
| 2001/0000529 A1 | 4/2001 | Ronnberg |

FOREIGN PATENT DOCUMENTS

| | | |
|---|---|---|
| EP | 0 196 654 A2 | 10/1986 |
| EP | 0 196 654 B1 | 10/1986 |
| EP | 0 238 200 A2 | 9/1987 |
| EP | 0 560 630 A1 | 9/1993 |
| GB | 2112267 | 7/1983 |
| SE | 9904202-0 | 11/1998 |

(Continued)

*Primary Examiner*—Tatyana Zalukaeva
*Assistant Examiner*—Ginger Chapman
(74) *Attorney, Agent, or Firm*—Buchanan, Ingersoll & Rooney PC

(57) ABSTRACT

Absorbent product of pants-like shape, such as incontinence pants, including an elastic waist portion, an absorbent element, and a liquidtight outer layer which is intended to enclose the absorbent element on at least that side thereof which faces away from the wearer during use of the article. The elastic waist portion is made from an elastic first piece which is essentially rectangular and is intended to form the rear portion and side portions of the pants-like product. A second piece forms the front portion and crotch portion of the pants-like product. The second piece is elongate, and the width thereof is, at least in the crotch portion, smaller than the length of the first piece. The second piece is arranged with its longitudinal direction at right angles in relation to the longitudinal direction of the first piece and is connected by a first end portion to one longitudinal edge portion of the first piece. One end portion of the first piece is connected to a first side edge portion of the second piece, and the other end portion of the first piece is connected to a second side edge portion of the second piece. The absorbent element is in its entirety arranged on the second piece.

13 Claims, 4 Drawing Sheets

FOREIGN PATENT DOCUMENTS

| | | |
|---|---|---|
| SE | 511 838 C2 | 12/1999 |
| SE | 513 374 C2 | 9/2000 |
| WO | WO 00/61049 | 10/2000 |
| WO | 01/15898 A1 | 3/2001 |
| WO | WO 01/13851 | 3/2001 |

* cited by examiner

ABSORBENT PRODUCT

This application claims priority under 35 U.S.C. § 119 to U.S. Provisional Application No. 60/302,365, entitled Absorbent Article and filed on Jul. 3, 2001, the entire content of which is hereby incorporated by reference.

TECHNICAL FIELD

The present invention relates to an absorbent product of pants-like shape, such as incontinence pants, nappy pants and sanitary towel pants or the like, comprising an elastic waist portion, an absorbent element, which has a length and a width and is intended to at least cover the genitals of the wearer during use of the article, and a liquidtight outer layer which is intended to enclose the absorbent element on at least that side thereof which faces away from the wearer during use of the article. The invention also relates to a method of manufacturing such absorbent products of pants-like shape.

BACKGROUND ART

Absorbent disposable products for taking up urine, feces or menstrual blood have developed greatly since they came into more general use during the 1960s and 1970s. As they are disposable products, it is necessary that they can be manufactured and sold at a very low price. At the same time, it is important that the products function well and reliably. Good fit and comfort are also important characteristics. The first disposable nappies included products having two parts, outer pants made of plastic, which were intended to be reused, and a rectangular absorbent insert which was disposable. The absorbent material in these inserts initially included cellulose tissue. Later, better absorption materials such as fluff pulp, which is made of cellulose, were developed. The fit and comfort of these early nappies were poor. The products were unwieldy and uncomfortable for the wearer. Towards the end of the 1970s, the first complete disposable nappies arrived, that is to say nappies in which the absorption cores were integrated with a liquidtight outer layer. The absorption materials had developed and improved, which resulted in the possibility of the absorption cores being adapted better to the anatomy of the wearer. Hourglass-shaped absorption cores with a narrower crotch portion between the two end portions are now the predominant shape in the industry. The trend has also been towards increasingly thin products, which has been made possible by the inclusion of what are known as superabsorbent materials in the absorption body. There are many reasons why thinner and even smaller absorption bodies are desirable. A thinner, smaller absorption body is more comfortable and more discreet, which is especially important for adult incontinent wearers. A reduction in volume may also be very important financially because the product then requires less storage space and is easier to transport and takes up less shelf space in shops. This is important for the financial management of the shops, and if a manufacturer can produce products requiring less space in the shops than the products of the competitors, this affords a not inconsiderable competitive advantage. Moreover, there is increased pressure from authorities, in particular as far as disposable articles are concerned, to use as little material as possible for the purpose of reducing the burden on the environment.

The smaller the absorption bodies become, the more important it becomes that the absorption bodies come to lie in the correct place directly in front of the genitals of the wearer and remain in place during use even when the wearer is very active and moves a great deal. The demands of consumers for discretion, comfort and reliable functioning are also increasingly exacting. Requirements for the absorption body to come to lie correctly when put on and then be retained in the correct place have therefore increased the need for good fixing of the product on the body and the need for very good adaptability to the body when the wearer moves, at the same time as requirements have increased for the product to always come to lie in the correct place when the article is put on the wearer. This has led to the development of what are known as nappy pants, which have elastic portions for improved fit and comfort and increased flexibility during movements of the wearer compared with conventional absorbent products.

An early patent publication relating to nappy pants of the disposable type is GB 2 112 267-A. However, this publication from 1983 discloses primitive nappy pants which did not become a commercial product. Not until the 1990s did absorbent products of pants-like shape and construction become a major commercial product. Pants-like products now exist in the form of nappies for infants and nappies for adults and to some extent sanitary towel pants for absorption of menstrual fluid. Previously commercially available nappy pants have been designed in principle like conventional nappies with a front portion and a rear portion and also an intermediate crotch portion, the front and rear portions being interconnected by a side seam between each leg opening and the waist opening of the pants. The nappy pants have been produced by plane nappy-like pieces being produced in a continuous web, the individual nappy pants being formed by nappy-like blanks being folded double and provided with said side seams to form nappy pants. These side seams project laterally from the finished product and are undesirable because they project and interfere with the fit of garments worn over the top. On account of their shape, they are visible through garments worn on top of the nappy pants and fitting closely around the body. They can also snag in clothing and even cause tears in nylon tights. Such projecting side seams can also chafe and give rise to pressure sores on wearers who spend a lot of time lying on their side.

WO 00/61049 has proposed improved nappy pants, in which the projecting sides seams have been eliminated. In this construction, the side seams have been eliminated by virtue of elastic side portions extending continuously in one piece from the front portion of the nappy pants to their rear portion on both sides of the nappy pants. However, the nappy pants according to WO 00/61049 have a number of disadvantages. The nappy pants according to said publication have what is referred to as a chassis, which extends over the entire nappy pants and forms the front portion, the crotch portion and the rear portion and is most reminiscent of a conventional nappy, and also said elastic side panels which each overlap the chassis at both the front and the rear on the nappy pants. These overlapping portions do not serve any actual purpose on the finished product and are in fact undesirable because a lot of material is wasted, that is to say they are used for no other purpose than joining together. The overlapping, joined-together portions are less of a nuisance and less uncomfortable for the wearer than the projecting side seams on previously known nappy pants. Owing to their unfavourable positioning, particularly at the rear, the overlapping portions can still give rise to a risk of chafing and back sores on wearers who spend a lot of time lying on their back. Another disadvantage of the nappy pants according to WO 00/61049 is that said chassis is relatively large and, as this portion is relatively rigid at least in comparison with the elastic side portions of the nappy pants, the nappy pants as a whole are not as adaptable to the body of the wearer but there is a risk that the nappy pants will be displaced from their optimum position in relation to the body when a wearer lies in bed and moves. In particular, the rigid rear portion of the nappy pants can be displaced and pull both the crotch portion and the front portion from their optimum positions directly in front of the genitals of the wearer because the front and crotch portion are essentially rigidly joined together in one piece with the rear portion.

DISCLOSURE OF INVENTION

By means of the present invention, an improved absorbent product of pants-like shape has been produced.

A product of the type referred to in the introduction is to this end characterized in that said elastic waist portion is made from an elastic first piece which is essentially rectangular in the extended state and is intended to partly surround the trunk of the wearer and to form the rear portion and side portions of the pants-like product, in that a second piece forming part of the product is designed to form the front portion and crotch portion of the pants-like product, in that said second piece is elongate with two opposite end edges and two opposite longitudinal edges, in that the width of the second piece is, at least in the crotch portion, smaller than the length of the first piece, in that the second piece is arranged with its longitudinal direction at right angles in relation to the longitudinal direction of the first piece and is connected by a first end portion to one longitudinal edge portion of the first piece, centrally thereon, in that one end portion of the first piece is connected to a first side edge portion of the second piece, and in that the other end portion of the first piece is connected in a corresponding manner to a second side edge portion of the second piece, in addition to which the absorbent element is in its entirety arranged on the second piece.

By virtue of the fact that the entire rear portion as well is elastic and, together with the elastic side portions, forms a single continuous elastic first piece, the pants as a whole are more adaptable to body movements. Local irregularities are taken up and smoothed out by the continuous elastic piece and are not transferred to the more rigid parts of the front portion and crotch portion located directly in front of the genitals of the wearer. Compared with conventional nappies and previously known absorbent products of pants-like shape, the product according to the present invention affords superior fit and comfort. Most of the pants-like garment is completely smooth. The seams required are arranged at the transition between the front portion and the first piece and at the transition between the first and the second piece in the crotch portion. These seams come to lie in places which are not subjected to any significant pressure during use of the product, and there is less risk of chafing and pressure sores caused by seams on the pants-like product.

The design of the absorbent product according to the invention in only two part pieces, where the absorbent element is in its entirety located on the second part piece, affords greater freedom of choice with regard to manufacturing method compared with previously known products of pants-like shape.

According to one embodiment, the invention is characterized in that the length of the second piece is greater than the width of the first piece, and in that the projecting portion of the second piece formed by the length difference is in its entirety located below that side edge of the first piece which is the lower one during use of the product, and there forms the crotch portion. According to one embodiment, the invention is in this connection characterized in that said projecting portion has a smaller width than the remainder of the second piece.

According to another embodiment, the invention is characterized in that the absorbent element extends in its longitudinal direction over the entire crotch portion and a little way up over the front portion in the direction of that side edge of the first piece which is the upper one during use of the product.

According to another embodiment, the invention is characterized in that the absorbent element is arranged so as to extend with its lower end portion only a little way over the crotch portion and over less than half the extent of said projecting portion. According to one embodiment, the invention is in this connection characterized in that the absorbent element tapers in the direction of the crotch portion and is essentially triangular in plane form.

According to an embodiment in which the absorbent element extends over the crotch portion, the invention is characterized in that the absorbent element forms a concave shape with its side edge portions in the crotch area.

According to another embodiment, the invention is characterized in that the second piece includes a liquid-permeable inner layer and a liquidtight outer layer, and in that the absorbent element is arranged between said inner and outer layers, the inner and outer layers extending in the lateral direction and longitudinal direction outside the absorbent element and being interconnected there.

According to one embodiment, the invention is characterized in that said connected side edge portions and end portions of said first and second pieces are, before connection, arranged in an overlapping manner, with the inside of an overlapping portion being arranged against the outside of an overlapped portion.

A method of manufacturing a product of the type mentioned in the introduction is characterized according to the invention in that said elastic waist portion is made from an elastic first piece which is essentially rectangular in the extended state and is intended to partly surround the trunk of the wearer and to form the rear portion and side portions of the pants-like product, in that a second piece forming part of the product is designed to form the front portion and crotch portion of the pants-like product, in that said second piece is elongate with two opposite end edges and two opposite longitudinal edges, in that the width of the second piece is, at least in the crotch portion, smaller than the length of the first piece, in that the second piece is arranged with its longitudinal direction at right angles in relation to the longitudinal direction of the first piece and is connected by a first end portion to one longitudinal edge portion of the first piece, centrally thereon, in that one end portion of the first piece is connected to a first side edge portion of the second piece, and in that the other end portion of the first piece is connected in a corresponding manner to a second side edge portion of the second piece. According to one embodiment, the method is in this connection characterized in that the absorbent element is in its entirety arranged on the second piece forming part of the product before said piece is connected to said first piece.

BRIEF DESCRIPTION OF DRAWINGS

The invention will be described in greater detail below with reference to illustrative embodiments shown in the accompanying drawings, in which.

Figure 1:
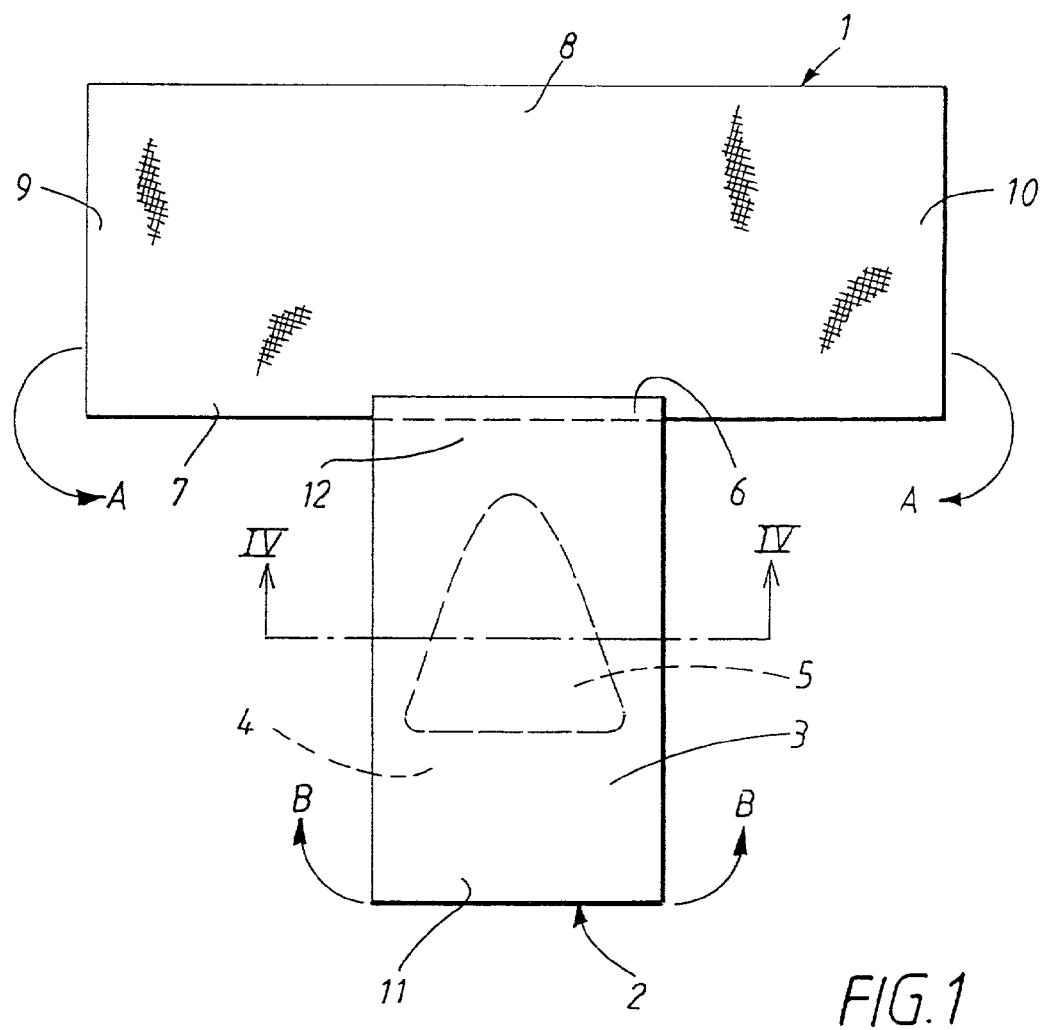
FIG. 1 shows diagrammatically a phase of the construction of an absorbent product according to a first embodiment.

As can be seen from FIG. 1, the product in the embodiment according to FIG. 1 comprises a first piece 1. This piece is elastically stretchable and is shown in FIG. 1 in a plane and even extended state, in which the elastic piece 1 is essentially rectangular. The elastic first piece 1 can be made from conventional materials well-known to the person skilled in the art, such as woven elastic materials, elastic non-wovens or elastic films. The important factor is that the elastic piece is stretchable for a wearer when the product is put on, and that it fits closely with suitable tightness around the wearer during use of the article. The tightness is of course regulated by means of size and elastic stretchability.

Figure 4:
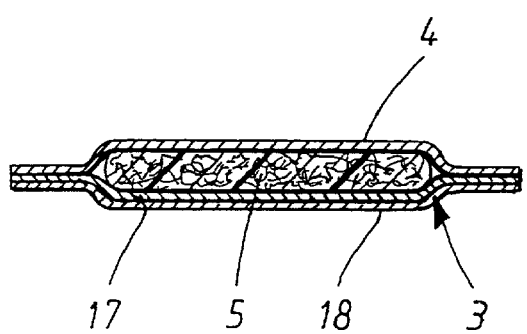
FIG. 4 shows a section along the line IV—IV in FIG. 1.

The product includes a second piece 2 which, as can be seen from FIGS. 1 and 4, comprises an outer layer 3, an inner layer 4 and an absorbent element 5 arranged therebetween. In the embodiment in plane form shown in FIG. 1, the element 5 is essentially triangular. The material selected for the absorption element is not critical, but it can be chosen from among materials or material combinations well-known to the person skilled in the art. For example, the absorbent element can include cellulose fluff pulp with superabsorbent materials in powder or fibre form added in. The outer layer 3 can include, for example, a polyethylene film of conventional type for absorbent products. A liquidtight film in combination with an outer fibre layer is suitable if an absorbent product with a more textile-like appearance is desired. The inner layer 4 may preferably be made from a liquid-permeable non-woven. The second piece 2 is elongate and is arranged with its longitudinal direction at right angles in relation to the longitudinal direction of the first piece 1. The second piece 2 is connected by one end portion 6 to one longitudinal edge portion 7 of the first piece, centrally thereon. The connection can be made by means of, for example, adhesive, thermal bonding or ultrasonic bonding.

Figure 2:
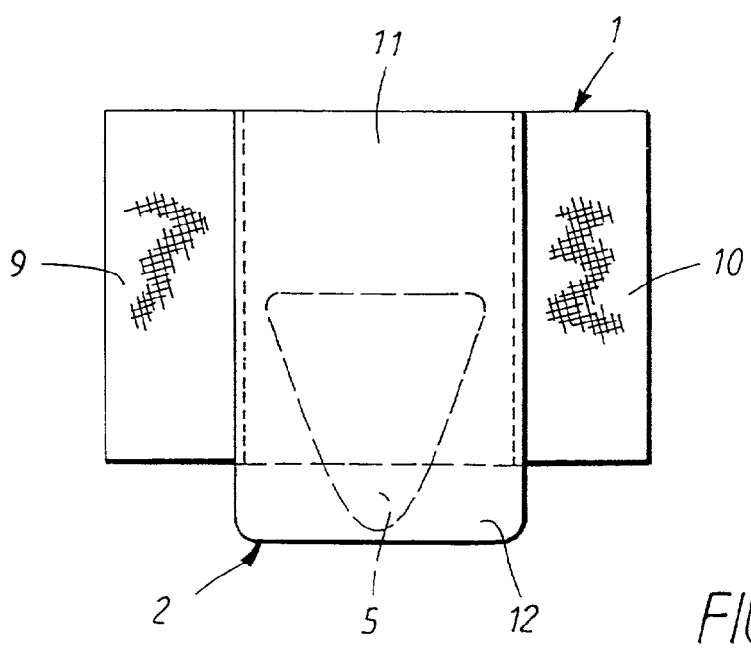
FIG. 2 shows diagrammatically in plane form an assembled product according to the first embodiment.
Figure 3:
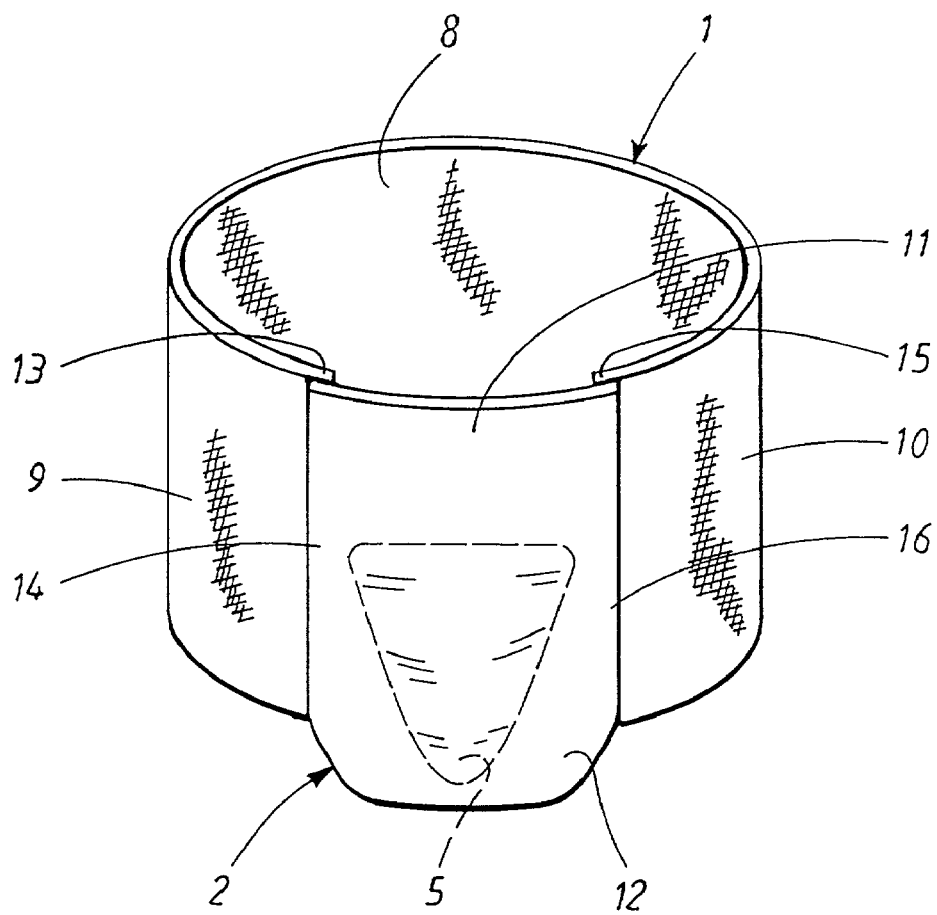
FIG. 3 shows the product according to FIG. 2 in perspective.

In FIG. 1, the arrows A and B illustrate how the first and second pieces are folded to form the absorbent product of pants-like shape shown in FIGS. 2 and 3. The elastic piece 1 is folded in according to the arrows A shown to form the rear portion 8 and side portions 9, 10 of the product, while the second piece is folded upwards according to the arrows B to form the front portion 11 and crotch portion 12 of the product.

As can be seen most clearly from FIG. 3, one end portion 13 of the first piece is arranged so as to be overlapped a little by a first side edge portion 14 of the second piece, and the other end portion 15 of the first piece is in a corresponding manner arranged so as to be overlapped a little by a second side edge portion 16 of the second piece. These overlapping portions are interconnected by means of, for example, adhesive, thermal bonding or ultrasonic bonding. Alternatively, the front portion and the crotch portion can be arranged detachably along said overlapping portions 13, 14 and 15, 16. Such a detachable connection can be made by means of, for example, hook means (not shown), as a result of which the pants-like product can be opened and subsequently reclosed with the same fit and tightness.

In FIG. 4, the thickness of the second piece has been exaggerated for the sake of clarity. The figure shows an outer layer 3 preferably including a laminate of a plastic film 17 and a non-woven layer 18 arranged outside. The inner layer 4 may preferably include a liquid-permeable non-woven of a type well-known to the person skilled in the art.

Figure 5:
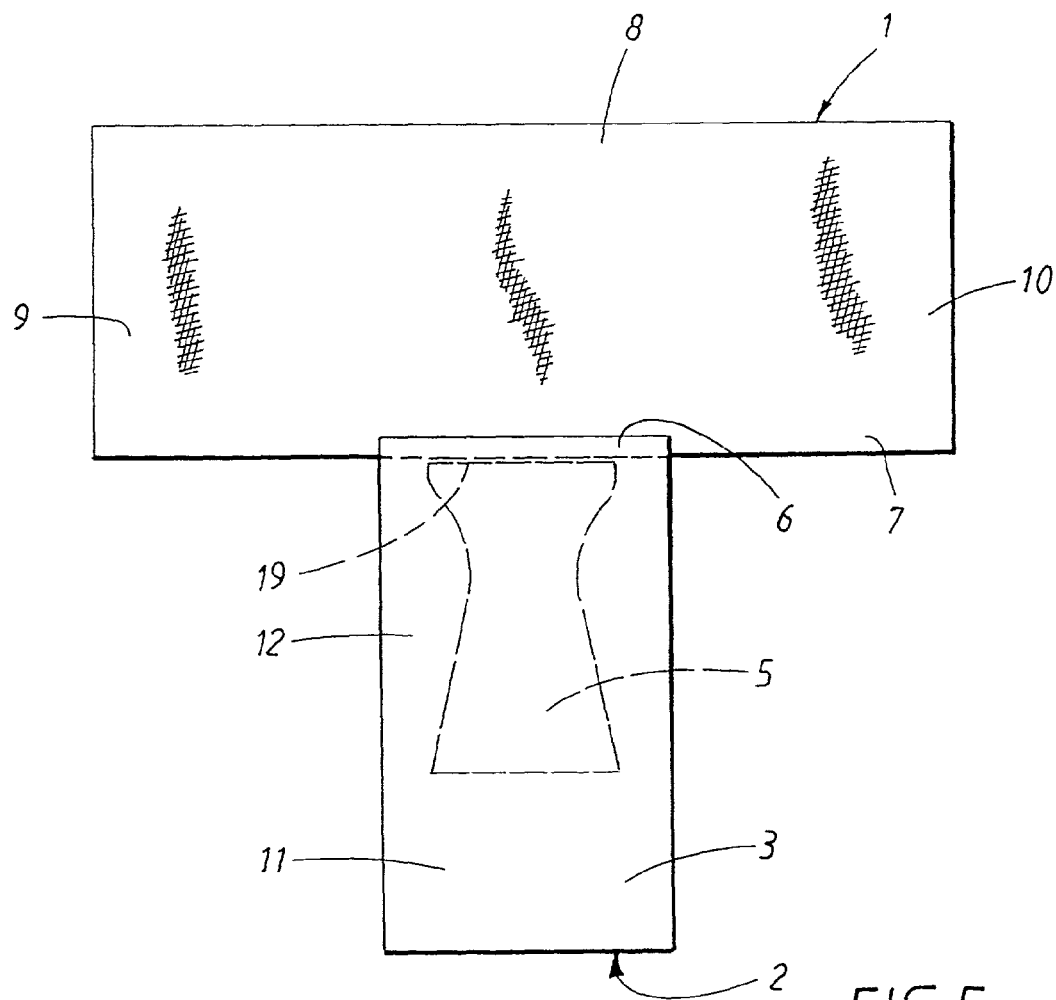
FIG. 5 shows diagrammatically a phase of the construction of an absorbent product according to a second embodiment.
Figure 6:
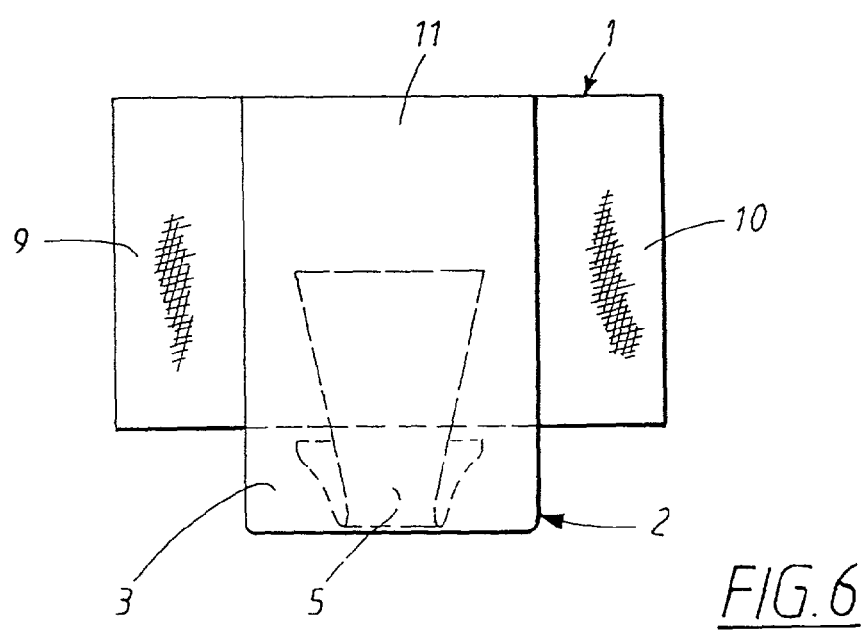
FIG. 6 shows in plane form an assembled product according to the second embodiment.

In the embodiment shown in FIGS. 5 and 6, those parts corresponding to the same parts in the embodiment according to FIGS. 1–4 have been provided with the same reference numbers. The only difference between the embodiment according to FIGS. 5 and 6 and that described above is the shape and extent of the absorbent element. In this second embodiment, the absorbent element 5 is hourglass-shaped in plane form, as can be seen most clearly from FIG. 5, the narrower portion being intended to be arranged in the crotch of the wearer during use of the product. The upper end edge 19 of the absorbent element 5 is located directly adjacent to the lower edge portion 7 of the first elastic piece, which means that the absorbent element according to this second embodiment extends over the entire crotch area and a little way up over the front portion 11, as can be seen from FIG. 6.

Figure 7:
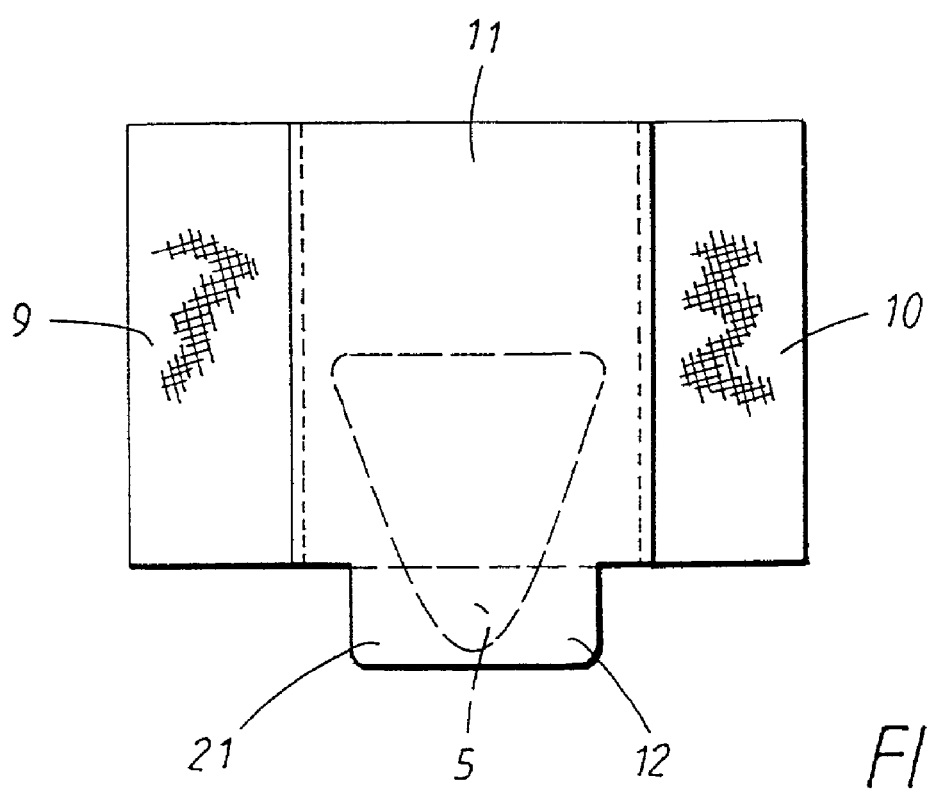
FIG. 7 shows in plane form an assembled product according to a third embodiment.

FIG. 7 shows a third embodiment which is slightly modified in relation to the first embodiment. The only difference is that a part piece 21 of the second piece is made narrower than the remainder of the second piece, in which way a pants-like product with a narrower crotch portion is obtained, as can be seen from FIG. 7.

The invention is not limited to the illustrative embodiments described above, but a number of modifications are possible within the scope of the patent claims below.

The invention claimed is:

1. Absorbent product of pants-like shape, comprising:
   an absorbent element having a length and a width for at least covering the genitals of a wearer during use of the absorbent pants product, and
   a liquidtight outer layer for enclosing the absorbent element on at least a side thereof which faces away from the wearer during use of the absorbent pants product,
   an elastic waist portion, said elastic waist portion including an elastic first piece which is essentially rectangular in an extended state for partly surrounding a trunk of the wearer and thereby forming a rear portion and side portions of the absorbent pants product, and
   a second piece forming a front portion and a crotch portion of the absorbent pants product, wherein said second piece is elongate with two opposite end edges and two opposite longitudinal edges, a width of the second piece being, at least in the crotch portion, smaller than a length of the first piece,
   wherein the second piece is arranged with its longitudinal direction at right angles in relation to the longitudinal direction of the first piece and is connected by a first end portion to one longitudinal edge portion of the first piece, centrally thereon, wherein one end portion of the first piece is connected to a first side edge portion of the second piece, and another end portion of the first piece is connected in a corresponding manner to a second side edge portion of the second piece,
   wherein the absorbent element is in its entirety arranged on the second piece,
   wherein the length of the second piece is greater than a width of the first piece, and a projecting portion of the second piece formed by the length difference is in its entirety located below that side edge of the first piece which is the lower one during use of the product, and thereby forms the crotch portion, and wherein the absorbent element is arranged so as to extend with its lower end portion only a little way over the crotch portion and over less than half the extent of said projecting portion.

2. Absorbent product according to claim 1, wherein said projecting portion has a smaller width than a remainder of the second piece.

3. Absorbent product according to claim 1, wherein the absorbent element tapers in the direction of the crotch portion and is essentially triangular in plane form.

4. Absorbent product according to claim 1, wherein the second piece includes a liquid-permeable inner layer and said liquidtight outer layer, the absorbent element being arranged between said inner and outer layers, and the inner and outer layers extending in the lateral direction and longitudinal direction outside the absorbent element and being interconnected there.

5. Absorbent product according to claim 4, wherein said connected side edge portions and end portions of said first and second pieces are, before connection, arranged in an overlapping manner, with an inside of an overlapping portion being arranged against an outside of an overlapped portion.

6. Absorbent product according to claim 1, wherein said absorbent product is selected from the group consisting of incontinence pants, nappy pants, and sanitary towel pants.

7. Absorbent product of pants-like shape, comprising:
an absorbent element having a length and a width for at least covering the genitals of a wearer during use of the absorbent pants product, and
a liguidtight outer layer for enclosing the absorbent element on at least a side thereof which faces away from the wearer during use of the absorbent pants product,
an elastic waist portion, said elastic waist portion including an elastic first piece which is essentially rectangular in an extended state for partly surrounding a trunk of the wearer and thereby forming a rear portion and side portions of the absorbent pants product, and
a second piece forming a front portion and a crotch portion of the absorbent pants product, wherein said second piece is elongate with two opposite end edges and two opposite longitudinal edges, a width of the second piece being, at least in the crotch portion smaller than a length of the first piece.
wherein the second piece is arranged with its longitudinal direction at right angles in relation to the longitudinal direction of the first piece and is connected by a first end portion to one longitudinal edge portion of the first piece, centrally thereon, wherein one end portion of the first piece is connected to a first side edge portion of the second piece, and another end portion of the first piece is connected in a corresponding manner to a second side edge portion of the second piece,
wherein the absorbent element is in its entirety arranged on the second piece,
wherein the length of the second piece is greater than a width of the first piece, and a projecting portion of the second piece formed by the length difference is in its entirety located below that side edge of the first piece which is the lower one during use of the product, and thereby forms the crotch portion, and
wherein the absorbent element extends in its longitudinal direction over the entire crotch portion and a little way up over the front portion in the direction of that side edge of the first piece which is the upper one during use of the product.

8. Absorbent product according to claim 7, wherein the absorbent element forms a concave shape with its side edge portions in the crotch area.

9. Absorbent product according to claim 7, wherein said absorbent product is selected from the group consisting of incontinence pants, nappy pants, and sanitary towel pants.

10. Absorbent product according to claim 7, wherein the second piece includes a liquid-permeable inner layer and said liquidtight outer layer, the absorbent element being arranged between said inner and outer layers, and the inner and outer layers extending in the lateral direction and longitudinal direction outside the absorbent element and being interconnected there.

11. Absorbent product according to claim 10, wherein said connected side edge portions and end portions of said first and second pieces are, before connection, arranged in an overlapping manner, with an inside of an overlapping portion being arranged against an outside of an overlapped portion.

12. Method of manufacturing an absorbent product of pants-like shape, such as incontinence pants, nappy pants or sanitary towel pants, comprising:
providing an elastic waist portion, an absorbent element, which has a length and a width and is intended to at least cover the genitals of the wearer during use of the article, and a liquidtight outer layer which is intended to enclose the absorbent element on at least that side thereof which faces away from the wearer during use of the article,
forming said elastic waist portion from an elastic first piece which is essentially rectangular in the extended state and is intended to partly surround the trunk of the wearer and form the rear portion and side portions of the pants-like product,
providing a second piece to form the front portion and crotch portion of the pants-like product, said second piece is elongate with two opposite end edges and two opposite longitudinal edges, the width of the second piece is, at least in the crotch portion, smaller than the length of the first piece, and the length of the second piece is greater than a width of the first piece.
arranging the second piece with its longitudinal direction at right angles in relation to the longitudinal direction of the first piece,
locating a projecting portion of the second piece formed by the length difference in its entirety below that side edge of the first piece which is the lower one during use of the product, thereby forming the crotch portion,
arranging the absorbent element so as to extend with its lower end portion only a little way over the crotch portion and over less than half the extent of said projecting portion,
connecting a first end portion of the second piece to one longitudinal edge portion of the first piece, centrally thereon,
connecting one end portion of the first piece to a first side edge portion of the second piece, and
connecting the other end portion of the first piece in a corresponding manner to a second side edge portion of the second piece.

13. Method according to claim 12, wherein the absorbent element is in its entirety arranged on the second piece forming part of the product before said piece is connected to said first piece.

* * * * *